(12) United States Patent
Rawson

(10) Patent No.: US 10,226,463 B2
(45) Date of Patent: Mar. 12, 2019

(54) FLUOROURACIL GLYCOLATE COMPOUND FOR THE TREATMENT OF WARTS, MOLLUSCUM CONTAGIOSUM

(76) Inventor: John Chesley Rawson, Damascus, OR (US)

( * ) Notice: Subject to any disclaimer, the term of this patent is extended or adjusted under 35 U.S.C. 154(b) by 103 days.

(21) Appl. No.: 13/506,097

(22) Filed: Mar. 26, 2012

(65) Prior Publication Data

US 2018/0098989 A1    Apr. 12, 2018

(51) Int. Cl.
*A61K 31/513* (2006.01)
*A61P 17/12* (2006.01)

(52) U.S. Cl.
CPC .......... *A61K 31/513* (2013.01); *A61P 17/12* (2018.01)

(58) Field of Classification Search
CPC .............................. A61K 31/513; A61P 17/12
See application file for complete search history.

(56) References Cited

PUBLICATIONS

Magic wart cream.com document, Mar. 22, 2010 and Feb. 12, 2008 downloaded from the internet on May 24, 2018, pp. 1-10 . URL:http://www.magicwartcream.com/Staff.html.*

* cited by examiner

*Primary Examiner* — Savitha M Rao
(74) *Attorney, Agent, or Firm* — Michael D. Eisenberg

(57) ABSTRACT

This is a disclosure for a prescription formulation of fluorouracil Glycolate: Magic Wart Cream. Its treatment regimen results in eradication of HP Group 1-6 virus warts and molluscum. The topical application of Magic Wart Cream with a toothpick to center of wart/molluscum, occlude with tape at bedtime, then mild abrasion with washing in the morning will over a period of 4 to 6 weeks lead to the expulsion of the wart/molluscum. The new chemical compound is unique and minimizes side effects and treatment failures.

6 Claims, 1 Drawing Sheet

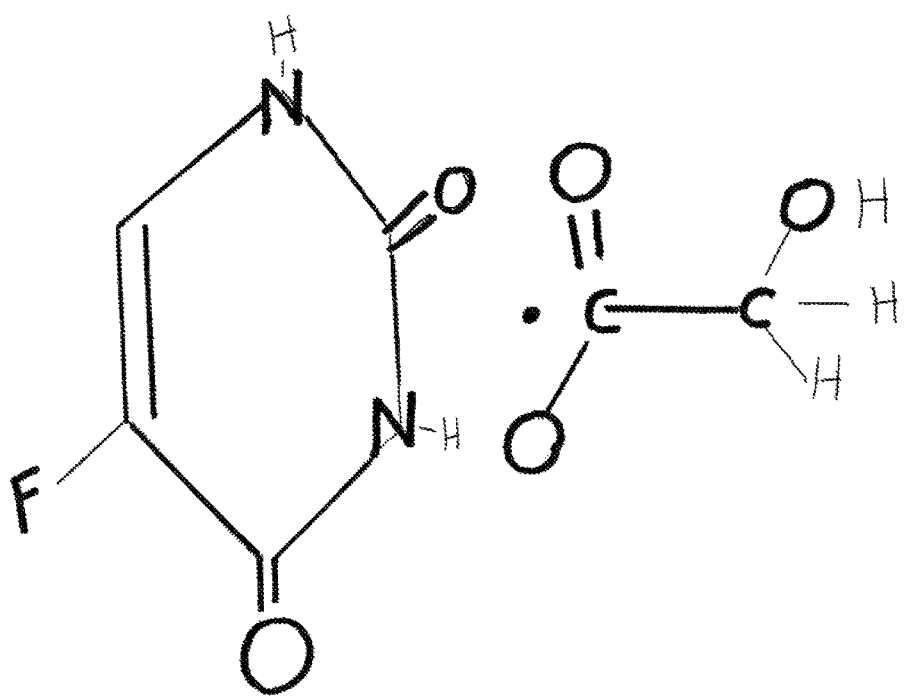

FLUOROURACIL GLYCOLATE COMPOUND FOR THE TREATMENT OF WARTS, MOLLUSCUM CONTAGIOSUM

CROSS-REFERENCE TO RELATED PATENT APPLICATIONS

The present patent application claims benefit from provisional patent application. No. 61/466,152, filed on Mar. 21, 2011, which is herein incorporated by reference.

BACKGROUND

The present invention relates to a new compound (dubbed magic wart cream) in the treatment of warts (molluscum contagiosum).

Human manifestation of external warts and molluscum are unsightly and confer not only psychological pain, embarrassment, and worry about appearance, but also physical symptoms that include itching, bleeding, cracking, oozing, and pain at the site of the lesion. Warts on molluscum lesions presenting on the face are particularly damaging to the developing psyche of pediatric patients who have to endure cruel derision and ridicule.

The different types of warts referred to as verrucae are subdivided according to the location on the body (on the hands, feet, genitals) and their morphological presentation. Many treatment options are routinely employed by physicians without success. Many of the in-office treatments can lead to the spreading of the viral lesions by activating the growth cycle of the virus.

Cryotherapy with liquid nitrogen is used by physicians to combat molluscum contagiosum. This treatment is painful and traumatizing to pediatric patients and has significant failure rate. Other treatments include activated t-lymphocyte stimulating treatments that include topical application of the following chemicals referred to as chemical sensitizers: squaric acid, squaric acid diethylester, dinitrochlorobenzene, dipenylcyclopropenone. Topical acid treatments are based on the application of acids such as bichloroacetic acid, trichloroacetic acid, retinoic acid, salicylic acid, lactic acid, pyruvic acid. These acid treatments act by attacking the high sulfur containing amino acids compromising keratin and by disrupting the adhesion of the keratinocytes.

The above treatments do not interrupt viral bioenergetics of cell division and the growth of the virus responsible for the wart lesions.

Intralesion injections for the treatment of molluscum contagiosum include *candida* allergenic extract and bleomycin. These treatments can be painful and are non-specific to the root cause of warts/molluscum.

Plant-based treatments and naturally-derived-product treatments include extracts of *podophyllum* (also known as American mandrake root or mayapple). The *Podophyllum* resin or purified fraction derived therefrom is used with cantharone treatments. The resulting composition is known ascantharone collodion or cantharone plus and contains cantharone with salicylic acid and *podophyllum* resin. This composition is in a vehicle of flexible collodion. The cantharone component, referred to as Beetle Juice, blister juice, or "Spanish Fly" upon application will cause a blister to form and resolve within 1-2 weeks and does not have a high success rate.

Treatments with idoxuridine or fluorouracil alone have been employed, but to limited degree due to the side effects encountered.

The above-mentioned treatments have a high rate of failure. Moreover, surgical office procedures are often very expensive and leave scars. Because of the high rate of treatment failures and the emergence of larger spreading warts as a result of ineffective treatments, there is a need for effective affordable prescription for home treatment for warts and molluscum.

BRIEF SUMMARY OF THE INVENTION

An aspect of some embodiments of the present invention relates to a cream for medical treatment of warts, comprising:

an active ingredient, fluorouracil glycolate, formed from a quantity of fluorouracil and a quantity of glycolic acid mixed and chemically reacted to form fluorouracil glycolate; and wherein the fluorouracil glycolate comprises a molecular weight of 205.72.

In a variant, the cream has concentration of fluorouracil glycolate between 1%-7% w/w.

In another variant, the cream further includes instructions for use of the cream.

In yet another variant, the cream comprises a biochemical mechanism of action which involves but is not limited to irreversible inhibition of hp group 1-6, viral thymidylate synthetase and Thymidylate synthetase methylatesdeoxyuridine monophosphate into Thymidine monophosphate.

In a variant, the cream is configured to treat any type of surface on a wart on humans and animals.

Another aspect of some embodiments of the present invention relates to a method for treating warts. The method includes: applying the above-mentioned cream to a center of a wart with a toothpick prior to a patient going to sleep; covering the wart with tape; and washing the cream off in the morning with soap and water. The cream contains fluorouracil glycolate as an active ingredient.

The formulation of Fluorouracil Glycolate (Magic Wart Cream) also involves 17 other ingredients which contribute to the efficacy of the topical pharmaceutical prescription product. The inventor has found that the other 17 ingredients synergize the efficacy and thereby accelerate the removal of the wart.

The novelty of this invention is based on the fact the Fluorouracil Glycolate compound of the present invention is unlike anything catalogued in organic/medicinal chemistry. Fluorouracil Glycolate results from a chemical reaction between fluorouracil and glycolic acid and this chemical reaction can proceed even at room temperature conditions without catalyst and occurs following the Lowry-Bronsted chemical reaction scheme.

The inventor has demonstrated the existence of the isolated compound Fluorouracil Glycolate and has performed melting point tests and infrared spectrophotometry to differentiate Fluorouracil Glycolate compound from the reactants and their relative melting points and spectrophotometric data. There are no special reaction conditions required for the formation of fluorouracil glycolate. It is an exothermic reaction and a small amount of heat is generated. It is also not possible to interrupt this reaction. Even if small amounts of fluorouracil and alphahydroxyacetic acid, glycolic acid are made to come into contact with one another, fluorouracil glycolate will be formed.

BRIEF DESCRIPTION OF THE DRAWINGS

FIG. 1 is the chemical formula of Fluorouracil Glycolate

DETAILED DESCRIPTION OF INVENTION

A cream (Magic Wart Cream) for the medical treatment of warts, comprising fluorouracil glycolate. The cream is a treatment for physicians to prescribe their patients desiring wart removal without painful or scarring surgical procedures. The cream is configured to treat a wart/molluscum on any type of surface on both humans and animals because it is not limited by host specificity.

The active ingredient in the cream is fluorouracil glycolate, which is produced by mixing together a quantity of fluorouracil and a quantity of glycolic acid. These two quantities chemically react to form the active ingredient. The fluorouracil glycolate has a molecular weight of 205.72 and its ending concentration is between 1%-7% w/w in the magic wart cream formulation.

The cream comprises instructions for use of the cream, where the treatment regimen requires specific adherence to the following prescription directions unless the physician wishes to modify the directions with respect to an individual circumstance. The specific directions or "sig" read: "Apply to the wart/molluscum center at bedtime with toothpick, Cover with tape, avoid applying to surrounding skin, wash off in the morning with soap and water, skip a day if tender."

The biochemical mechanism of action of the cream involves but is not limited to irreversible inhibition of hp group 1-6; viral thymidylate synthetase, which blocks synthesis of viral prymidine thymidine, which is needed for nucleotide replication; and thymidylate synthetase methylatesdeoxyuridine monophosphate into Thymidine monophosphate.

The fluorouracil glycolate causes scarcity in viral deoxythymidine monophosphate which causes cell death via thymidine-less death.

In the wart cream treatment of the present invention, the virus uptakes the fluorouracil glycolate into their cellular structure causing viral death and the wart/molluscum lesion sloughs off, resulting in wart removal. That treatment is Magic Wart Cream which contains a new unique compound fluorouracil glycolate in a topical treatment regimen available only with a prescription from a licensed practicing Physician. The daily application of the magic wart cream, with a toothpick to the center only of the wart at bedtime under tape, we have routinely observed expulsion or eradication of warts and molluscum within 4-6 weeks. It also comes with great reproducibility. In some cases, we have observed treatment success within a few days. The product is the invention of John Chesley Rawson, Pharmacist and Formulator, at Flanders Pharmacy located at 9124 SE Saint Helen's Street in Clackamas, Oreg. 97015.

Fluorouracil Glycolate is formed by a chemical reaction between fluorouracil and glycolic acid, in an acid-base reaction under the Lowry-Bronsted model in a typical acid-base reaction. The new unique compound when formed is stable at room temperature for approximately one year. The molecular weight of the new compound is 205.72. The magic wart cream formulation, a thick cream resembling peanut butter, has a consistency designed for easy application to the lesions with a toothpick. This is to eliminate any messy, troublesome dribbling as this was a problem encountered early and then overcome on a trial and error basis, resulting in the thicker consistency. By applying the magic wart cream to only the center of the wart, and not to the edges, it focuses the target of the high-sulfur containing, amino acid rich matrix of keratin to where the fluorouracil glycolate can pool. Then it forms a depot within the small socket of the lesion. This dictates the nature of the liberation absorption and distribution the drug delivery system. The unique properties of fluorouracil glycolate allows the saturation of the lesion without observed systemic absorption.

Method of Preparation:

The method of preparation involves weighing out a desired amount of moles of fluorouracil (m.w.=130.77), and an equimolar amount of glycolic acid (m.w.=76.05). The Fluorouracil powder is mechanically reduced in particle size, being careful not to create a powder cloud by means of enclosing the mechanical grinder in a hood within a large plastic enclosure. Once the grinding is complete, the powder is re-weighed for accuracy and then the calculations are made for an equimolar amount of glycolic acid. Indeed, through trial and error, it was observed that an excess of glycolic acid was necessary for completion of the reaction.

The fluorouracil is then added to a reaction vessel containing propylene glycol and brought to a temperature of 70 degrees Celsius. In an enclosed area with a magnetic stirrer the fluorouracil-propylene glycol is held constant for 45 minutes. The resultant mixture is somewhat cloudy but uniform in consistency. Some problems were encountered when the temperature was above 70 degrees Celsius, with crystalline polymorphs and pleomorphs around the edges of the reaction vessel. At temperature below 70 degrees Celsius, the ensuing reaction did not proceed to completion, perhaps due to an insufficient energy of activation. Then to obtain the fluorouracil-propylene glycol mixture, the appropriate amount of glycolic acid was slowly added to the reaction vessel so that the temperature did not rise above 70. This method was arrived at by trial and error, when adding too much glycolic acid too quickly caused a precipitous rise in temperature, deleterious to the formation of the desired product. The reactions was allowed to proceed for 1.5 hours, which at the time the appearance was clear liquid. While still at 70 degrees Celsius, calculations were made for incorporation into the vehicle which was retained at room temperature. The reaction product was slowly added to the special vehicle with a mechanical mixer until a uniform cooled mixture was achieved. After 15 minutes, the dermatological formulation was complete.

REFERENCES

1. Buck, H W Jr. (2007) warts genital BMJ clinical evidence.
2. Kodner, Chas M &Nasraty, Soraya (2004) Am Fam Physician
3. Salk, R S, Grogan K A Chang J J (2006) J Drugs Dermatology
4. Young, S, Cohen G E (2005) J Am Podiatry Med. Assoc.

I claim:

1. A cream for medical treatment of warts, comprising: an active ingredient, fluorouracil glycolate, formed from a quantity of fluorouracil and a quantity of glycolic acid mixed and chemically reacted to form fluorouracil glycolate; and
   wherein the fluorouracil glycolate comprises a molecular weight of 205.72.

2. The cream of claim 1, wherein having a concentration of fluorouracil glycolate between 1%-7% w/w.

3. The cream of claim 1, further comprising instructions for use of the cream.

4. The cream of claim 1, wherein the cream comprises a biochemical mechanism of action which involves but is not limited to irreversible inhibition of hp group 1-6, viral thymidylate synthetase and Thymidylate synthetase methylates deoxyuridine monophosphate into Thymidine monophosphate.

5. The cream of claim 1, wherein the cream is configured to treat any type of surface on a wart on-humans and animals.

6. A method for treating warts, comprising:
applying the cream of claim 1 to a center of a wart with a toothpick prior to a patient going to sleep;
covering the wart with tape; and
washing the cream off in the morning with soap and water;
wherein the cream contains fluorouracil glycolate as an active ingredient.

\* \* \* \* \*